US008617487B2

(12) United States Patent
Plante et al.

(10) Patent No.: US 8,617,487 B2
(45) Date of Patent: Dec. 31, 2013

(54) SALIVA SAMPLE COLLECTION SYSTEMS

(75) Inventors: James Plante, La Jolla, CA (US); David Becker, San Diego, CA (US); Edgar MacBean, San Diego, CA (US); Kathryn J. Elliott, San Diego, CA (US)

(73) Assignee: Venture lending & Leasing VI, Inc., Portola Valley, CA (US)

( * ) Notice: Subject to any disclaimer, the term of this patent is extended or adjusted under 35 U.S.C. 154(b) by 1225 days.

(21) Appl. No.: 12/383,535

(22) Filed: Mar. 25, 2009

(65) Prior Publication Data

US 2012/0325721 A1 Dec. 27, 2012

(51) Int. Cl.
*B01L 3/00* (2006.01)

(52) U.S. Cl.
USPC ............ 422/430; 422/50; 422/501; 422/502; 422/503; 422/536; 436/180

(58) Field of Classification Search
USPC ............ 422/50, 430, 501–503, 536; 215/44; 436/180
See application file for complete search history.

(56) References Cited

U.S. PATENT DOCUMENTS

| | | | |
|---|---|---|---|
| 3,062,212 A | 11/1962 | Kravitz et al. | |
| 3,446,342 A * | 5/1969 | Michel | 206/232 |
| 3,814,097 A | 6/1974 | Ganderton et al. | |
| 3,832,141 A | 8/1974 | Haldopoulos et al. | |
| 3,846,077 A | 11/1974 | Ohringer et al. | |
| 4,209,488 A | 6/1980 | Breno | |
| 4,644,807 A | 2/1987 | Mar | |
| 4,682,689 A * | 7/1987 | Pereira et al. | 206/222 |
| 4,895,808 A | 1/1990 | Romer | |
| 5,040,678 A | 8/1991 | Lenmark, Sr. et al. | |
| 5,082,631 A | 1/1992 | Lenmark et al. | |
| 5,099,857 A | 3/1992 | Baldo et al. | |
| 5,268,148 A | 12/1993 | Seymour | |
| 5,422,018 A * | 6/1995 | Saunders et al. | 210/787 |
| 5,512,439 A | 4/1996 | Hornes et al. | |
| 5,674,456 A | 10/1997 | Chess et al. | |
| 5,981,293 A | 11/1999 | Charlton | |
| 6,537,264 B1 | 3/2003 | Cormier et al. | |
| 6,565,532 B1 | 5/2003 | Yuzhakov et al. | |
| 6,921,087 B2 * | 7/2005 | Takahashi et al. | 277/628 |
| 7,029,627 B2 | 4/2006 | Alley | |
| 7,303,212 B2 | 12/2007 | Arway et al. | |

(Continued)

OTHER PUBLICATIONS http://www.dnagenotek.com/US/news+events/pressrelease2008-10-11.html.

(Continued)

*Primary Examiner* — Jyoti Nagpaul
(74) *Attorney, Agent, or Firm* — Knobbe Martens Olson & Bear LLP

(57) ABSTRACT

Saliva sample collection systems are configured with special attention to ease-of-use for the unskilled user and safe transport and delivery by a conventional delivery services such as Federal Express. A sealed cavity is formed by tight coupling of two primary elements: a receiving vessel element and a sealing cap element. The receiving vessel has integrated therewith: a standing means, a fill-line window, a funnel system, a knife, a threadset, and containment tube among others. A complementary cap element includes a cooperating threadset, label receiving surface, gripping surface, seal means and reservoir with piercable thin-film membrane. These two primary elements may be accommodated in an application-specific shipping container which support two shipping modes whereby the system may be shipped safely to and from a donor user each way in a different shipping mode.

2 Claims, 4 Drawing Sheets

(56) References Cited

U.S. PATENT DOCUMENTS

| | | |
|---|---|---|
| 7,377,383 B2 | 5/2008 | Henry et al. |
| 7,378,054 B2 | 5/2008 | Karmali |
| 7,387,899 B1 | 6/2008 | D'Angelo |
| 7,387,999 B2 | 6/2008 | D'Oosterlynck |
| 2001/0002012 A1* | 5/2001 | Yeaton et al. ............ 215/44 |
| 2005/0164408 A1 | 7/2005 | Boss et al. |
| 2008/0227210 A1 | 9/2008 | Smith |
| 2009/0062753 A1 | 3/2009 | Ma |

OTHER PUBLICATIONS http://www.dnagenotek.com/US/news+events/pressrelease2008-11-10.html.

* cited by examiner

SALIVA SAMPLE COLLECTION SYSTEMS

BACKGROUND OF THE INVENTIONS

1. Field

The following invention disclosure is generally concerned with kits and systems for collection of biological matter and more specifically concerned with saliva collection, storage and transmission systems configured for non-expert use.

2. Prior Art

Container arts and engineering presently enjoys an advanced state whereby container design and function is configured for particular purpose. For example, and orange juice container made from cardboard may have incorporated features therein specifically designed for the acidic nature of orange juice which is quite different from attributes of similar cardboard containers designed for milk for example. In each case, particulars relating to shelf life, exposure to UV damage, pulp content, in example, affects design of a high-performance container system having a specific application.

Containers designed for nonfood applications also are highly advanced with many incorporated features designed to cooperate with the nature of the service for which it is designed. This is particularly true for containers designed to collect biological material and even more particularly when those containers are to be used without assistance from experts—i.e. for use by untrained consumers in a setting where professionals may not be present. Further such containers must sometimes support special features for long-term storage, durability, safe handling, transmission via postal and delivery services, among others.

In some special cases, it is desirable to provide a container suitable for safe transmission of biological matter via the mails and private delivery services. For example, packages may be arranged with a view towards use with private delivery systems and services such as those provided by Federal Express company. In this regard, a package system must be provided to protect against shock, temperature changes, duration, et cetera—those attributes associated with the normal procedures used by delivery service companies. It is further desirable that containers are designed for ease of use by non experts without need for special training—and without complex instructions and procedures. In certain applications, containers for collection of biological samples are to be used by a donor without assistance of experts or medical professional. In home collection systems, the container must be highly functional without complex instructions and further it must be devoid of failure mechanisms which tend to render collection of a sample defective. Thus, containers which effectively capture a sample with a minimal amount of steps and a minimal number of parts is a great benefit with respect to system success.

A number of systems have been developed for handling viscous liquids, particularly saliva and blood serum. See, for example, Haldopoulos, U.S. Pat. No. 3,832,141; Ohringer, U.S. Pat. No. 3,846,077; Breno, U.S. Pat. No. 4,209,488; Mar, U.S. Pat. No. 4,644,807; Romer, U.S. Pat. No. 4,895,808; and Seymore, U.S. Pat. No. 5,268,148. However, those apparatus that have previously been developed in this field are generally sophisticated devices intended for use by a skilled laboratory technician.

D'Angelo teaches in U.S. Pat. No. 7,387,999 dated Jun. 17, 2008 a saliva sample collection system. A sponge portion is used to swap saliva and saliva is thereafter extracted from the sponge by squeezing or centrifuge.

In a disclosure entitled "Apparatus for Sampling, Storing, Preserving and Testing a Specimen", inventor Alley of Pennsylvania presents a swab tip and cooperating container system which is arranged to compress the swap when inserted therein. A portion of the sample is conveyed into a plurality of separate chambers provided to isolate each from the others. As the kit is designed around multipurpose functions related to testing directly within the device, the complexity is significant. In applications where only a single sample is required, or systems where testing is done wholly external to the sample collection kit, this system does not provide advantage.

In U.S. Pat. No. 5,981,293, a full description for a fluid collection kit and method is published. Biex Inc, of California as assignee uses a fluid collection, filtration and storage device in connection with biological matters such as saliva, among others. In particular, the device has a first tube with a closed first end and open second end, and a second concentric tube acting in concert therewith. Also, the system deploys a cap to form a liquid tight seal at the outer tube orifice.

Inventors Chess et al, present their invention in U.S. Pat. No. 5,674,456 of Oct. 7, 1997. A container with specific design directed to a 'transportable container' for a medical specimen—takes the design of a 'Coplin' jar. "A lid hingedly coupled to the top of the jar" accommodates both 'open' and 'closed' positions. Included in these systems is a tray which receives the container in a "sideways fashion". However, this tray does not support a dual-mode accommodation for the jar.

Minnesota inventors Lenmark Sr. and Koentopp teach a specialized kit particularly suited for shipping transport. The container provides for a foam member with prescribed cut-outs to receive sample containing vials therein. While these cut-outs are not designed in support of any dual-mode shipping objectives, they do indeed accompany a plurality of elements in an application specific shipping box.

One kit manufactured by DNA Genotech Co. of Ontario, Canada is quite widely used by many professionals of the DNA diagnostics industries. However these systems have many complexities and shortcomings which contribute to failure mechanisms resulting in a unreliable system. A first important shortcoming of the Genotech system is that it is comprised of four discrete parts which must repeatedly be coupled and decoupled in a series of complex steps which must be executed in a particular order. While the kit includes a detailed instruction booklet in six languages with a series of grayscale photo-like diagrams, the steps illustrated are difficult to execute without error for some users.

In one important example, a receiving vessel is coupled by way of a thread set to a funnel element. The funnel is provided so that a user can easily spit into the device and the received saliva will be conveyed into the small aperture of the receiving vessel. After a sufficient quantity of saliva is received into the vessel, the funnel must be decoupled from the receiving vessel by twisting the funnel about an axis in a rotational direction opposite to that of which the vessel is twisted. However, this must be done only after a special DNA preserving and stabilizing fluid is introduced to the receiving vessel. To effect this, another thread set system is coupled to the funnel at an opposing end. That is, at the large end of the funnel, a specifically prepared container of fluid is screwed onto the funnel at its top. As the container is applied in this way, a membrane is pierced and fluid released into the funnel through which it passes and finally received into the receiving vessel to mix with the saliva. Then, the funnel may be finally decoupled from the receiving vessel. Thereafter, a stopper cap with a thread set identical to that of the funnel's narrow end is screwed onto the vessel aperture end to form a seal thereby trapping and containing both collected saliva and stabilization fluid therein.

The funnel and large cap/container are left as waste material. The reservoir contains residue chemicals which tend to cause anxiety in some persons. While it is not necessary to discard these pieces as medical waste, these leftover parts tend to at least have the appearance of medical waste and thus give rise to worry and a need for special and sometimes expensive treatment. It is surely preferable to devise a system with no leftover parts to be discarder as medical waste. Because the funnel needs to be coupled to and decoupled from the receiving vessel, it is formed with integrated finger grips which are easily engaged and ergonomically cooperative with human finger tips. However if the requirement that the funnel be screwed 'on' and 'off' the receiving vessel were removed, then so would the need for these finger grips; thus simplifying manufacturing processes and saving material. Another important problem with the collection systems described relates to spilling. Because a considerable amount of saliva is required to properly fill the receiving vessel, it generally takes a user some time to provide this quantity. During the process of filling the container, one may wish to set it down while time passes for additional saliva to form in the mouth. However, due to another design shortcoming, the device must continuously be held and cannot easily be put down without spilling its contents. It would be yet another important improvement if the container could rest on its own structure to allow a user time to fill the apparatus without having to continuously hold the device.

While systems and inventions of the art are designed to achieve particular goals and objectives, some of those being no less than remarkable, inventions of the art have limitations which prevent uses in new ways now possible. Inventions of the art are not used and cannot be used to realize the advantages and objectives of the invention taught herefollowing.

SUMMARY OF THE INVENTION

Comes now, James Plante, David Becker, Kathryn J. Elliott, and Edgar MacBean with an invention of saliva sample collection systems including devices particularly configured for ease-of-use by unskilled users and further configured for safe conveyance via standard shipping services. It is a primary function of these systems to provide easy-to-use saliva sample collection kits for direct-to-consumer use. It is a contrast to prior art that systems first taught and presented here do not require special training or skill to effectively use.

An apparatus for saliva sample collection, temporary storage and conveyance via delivery services is formed of two primary elements—each of these two elements having a plurality of features integrated therewith. Preferably formed of plastic in molding processes, these two elements cooperate together to provide 'coupled' and 'decoupled' states. A receiving vessel and sealing cap which couple together in best versions via mechanical interlock, in example a thread set type coupling, form a liquid tight containment cavity suitable for long-term and durable storage of a DNA in a saliva sample.

A receiving vessel may be provided include an integrated funnel portion which allows ergonomic cooperation with the human mouth with regard to spitting and efficiently receives saliva from a donor as the donor spits into a large aperture of the funnel at its top end. The funnel terminates at a narrow, generally cylindrical tubular portion suitable for containing liquids received therein.

A receiving vessel additionally has integrated therewith an outer body portion which forms a rigid standing means upon which the system may rest upright on flat surfaces. This outer body portion may support additional structure such as a viewing window and indicia. A receiving vessel may also include an integrated knife element.

A sealing cap has integrated therewith a seal mechanism, piercable liquid reservoir, grip surface, label receiving surface, among others.

When a cap element is coupled to a receiving vessel, the action of forming a seal therewith additionally causes breach to the integrity of the liquid reservoir such that the reservoir contents are released into and mix with matter already in the receiving vessel while at the same time forming a seal between the receiving vessel and the sealing cap such that no liquid can escape containment.

An auxiliary element of these systems is also included in some versions. An application-specific shipping container provides two operational modes for shipping and delivery of these devices. That is, the shipping container supports containment of a receiving vessel and sealing cap held separate from each other in a 'decoupled' state, and additionally provides for containment of a receiving vessel and sealing cap in a 'coupled' state. In a shipping mode characterized as a 'decoupled' state, the device is shipped to a user/customer. In a shipping mode characterized as a 'coupled' state the system is returned shipped to a laboratory for analysis. Thus this invention additionally contemplates cooperative shipping facility arranged as special-purpose shipping containers designed to further support the tasks and objectives particular to direct to consumer saliva sample collection.

OBJECTIVES OF THE INVENTION

It is a primary object of this invention to provide saliva sample collection systems.

It is an object of this invention to provide saliva sample collection systems which are easy to operate by untrained users without special skill.

It is a further object to provide self-contained saliva sample collection systems which do not leave waste by products after use.

It is an object of this invention to provide saliva sample collection systems which cooperate with a dual-mode application specific shipping container.

It is also an objective to provide systems of reduced parts and increased ease of use for improved reliability.

A better understanding can be had with reference to detailed description of preferred embodiments and with reference to appended drawings. Embodiments presented are particular ways to realize the invention and are not inclusive of all ways possible. Therefore, there may exist embodiments that do not deviate from the spirit and scope of this disclosure as set forth by appended claims, but do not appear here as specific examples. It will be appreciated that a great plurality of alternative versions are possible.

BRIEF DESCRIPTION OF THE DRAWING FIGURES

These and other features, aspects, and advantages of the present invention will become better understood with regard to the following description, appended claims and drawings where:

PREFERRED EMBODIMENTS OF THE INVENTION

Figure 1:
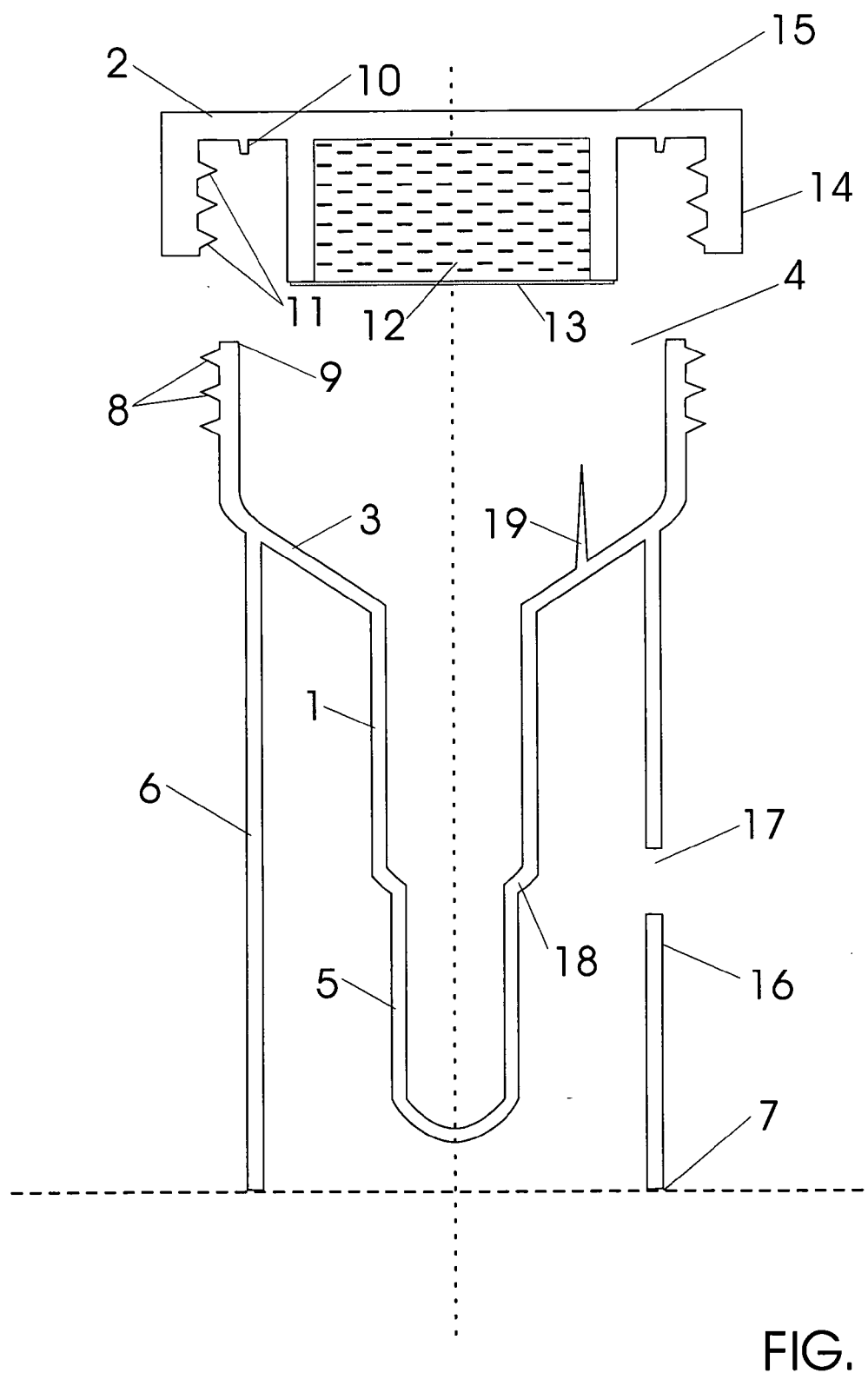
FIG. 1 is a cross-section view of a first version of one saliva sample collection system.

With attention to the appended drawing FIGS. 1-4 and particularly reference numerals therein, one gains a firm and complete understanding of system apparatus of these teachings.

Specifically, FIG. 1 illustrates in cross-sectional view of two primary elements in a spatially proximate relationship on a symmetry axis. A receiving vessel 1 is a complement part to a sealing cap 2—as these are arranged such that their geometries cooperate and include means for tight coupling with respect to each other. The receiving vessel element includes an integrated funnel portion 3 with an entrance aperture 4 and elongated cylindrical tubular portion 5 which lies coaxially with respect to a second cylindrical structure a rigid body 6 including terminus surface 7, for example an annulus, lying in a plane forming a 'foot' or 'base'. At the top of the receiving vessel element at an outside peripheral edge, a thread set system 8 is formed as a part of a coupling means between the receiving vessel element and the cap element. This coupling may further include a well-designed seating surface 9 to cooperate with an annular flange 10 integrated with the sealing cap to form a liquid tight seal. While preferred versions include those where the flange is molded integrally with the cap, other version include those where pressure fit receiving space holds an 'O'-ring to the sealing cap interior. When a sealing cap arranged accordingly is coupled with the receiving vessel, the cap forms a more durable liquid-tight seal with the receiving vessel at the 'O'-ring and corresponding and cooperating seat. A complementary and cooperating thread set 11 is formed on an inside cylindrical surface of the cap. When a cap so described and receiving vessel similarly so, are brought together and rotated about an axis in opposing directions, a liquid tight seal is formed between them as the threads are arranged such that the annular flange is pressure fitted to the seating surface of the receiving vessel. In addition to forming a liquid tight seal between the cap element and the receiving vessel element, the act of bringing these two elements together via this threaded coupling invokes another important function. A liquid tight reservoir 12 contains therein a special formula which operable to stabilize and preserve a biological sample such as saliva. The reservoir is comprised in part of one surface which may be pierced or otherwise compromised such as a thin-film membrane or foil 13. When the cap is screwed onto the receiving vessel it advances in an axial direction towards the receiving vessel. A carefully positioned knife 19 integrated with the receiving vessel is provided to pierce the membrane and cause the liquid therein to leave via gravity. Accordingly, bringing the cap into relation with the receiving vessel assures release of the formula from the reservoir and further assures it mixes with the collected and contained saliva thereby preserving it. The cap element may additionally include a knurled outer surface 14 and label receiving surface 15. The knurled outer surface promotes ease-of-use by permitting good ergonomic cooperation with the human fingers whereby the cap may be tightly coupled to the receiving vessel despite some resisting pressure due in-part to friction between the thin film membrane and knife and further the annular flange and its seat. The label receiving surface is adopted to accept by way of adhesives a label so that these containers might more easily be marked with identifying information. It is generally convenient to associate the contents of a used container with a particular donor and sometimes this is done by way of a label affixed to the cap which does not easily separate therefrom and remains quite accessible for every person in the processing chain.

Finally, the receiving vessel element may additionally have integrated therewith indicia 16 in support to promote ease-of-use. A "fill-line" mark can be included on the tubular cylindrical portion of the receiving vessel or other outside surface of the body. Other indicia may be also provided to similarly promote proper use.

In some preferred versions, a slot may be provided in the body to effect a viewing window 17 by which a user may view more easily the tubular portion which contains sample matter (saliva) being collected. More precisely, to view a ridge 18 formed into the tubular portion which operates as a fill-line or fill-limit.

With a clear understanding of each of these systems integrated with either of the two primary elements, the receiving vessel element or the cap element, a more detailed description of each follows as various versions are further described.

Figure 2:
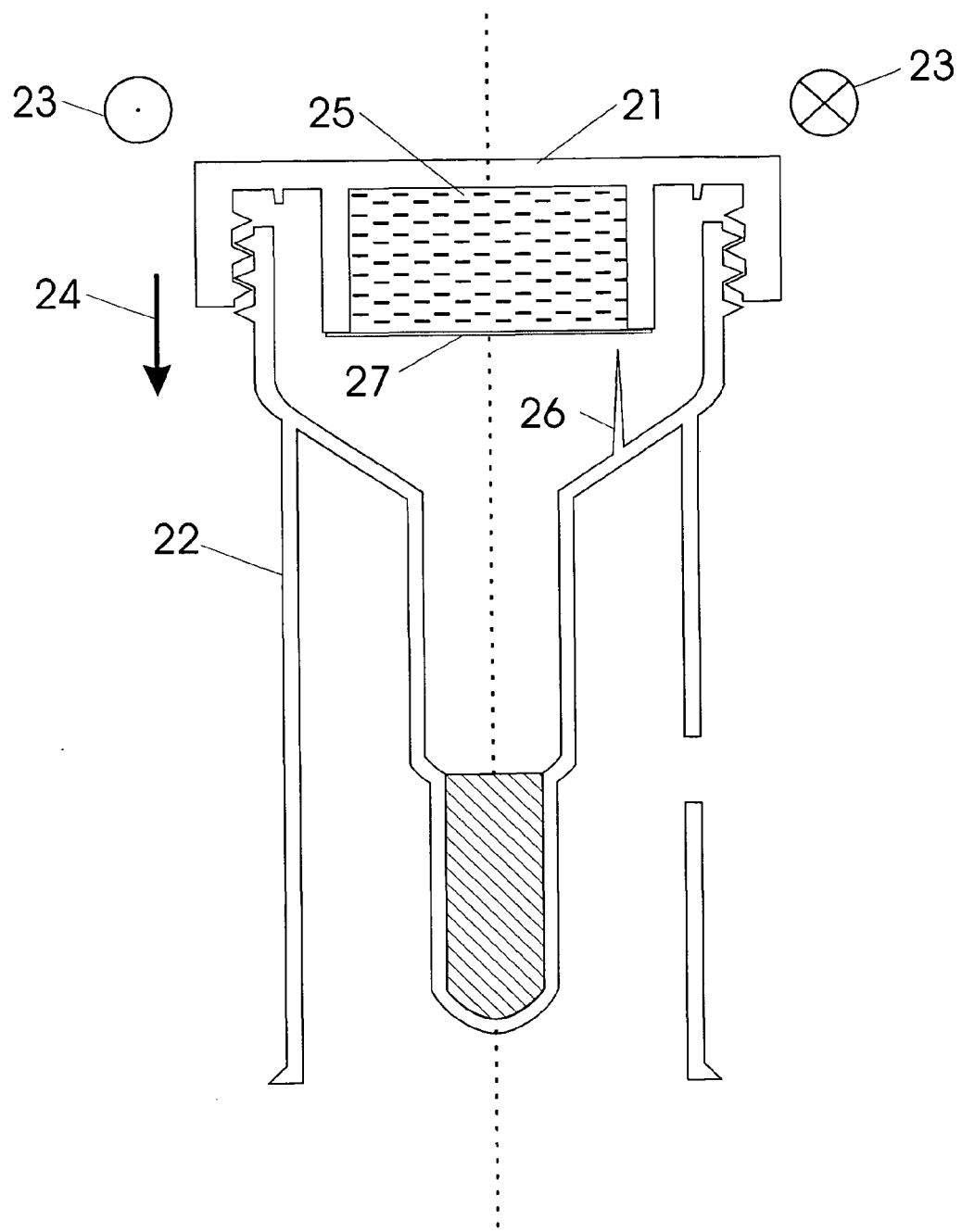
FIGS. 2 and 3 illustrate a cap being coupled to a receiving vessel via a thread set to cause a reservoir membrane to be punctured releasing fluid into the receiving vessel; and, FIG. 4 presents one version of a dual-mode shipping container system.
Figure 3:
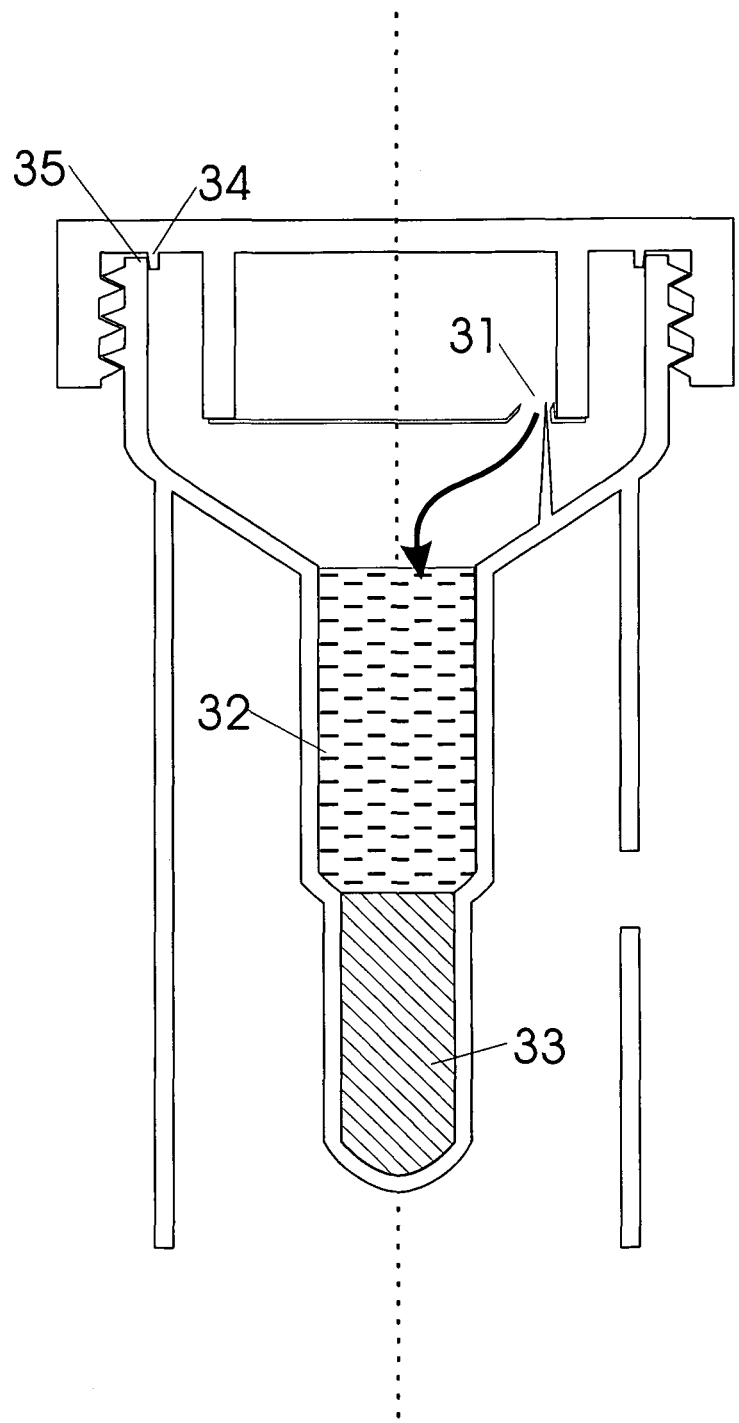
Figure 4:
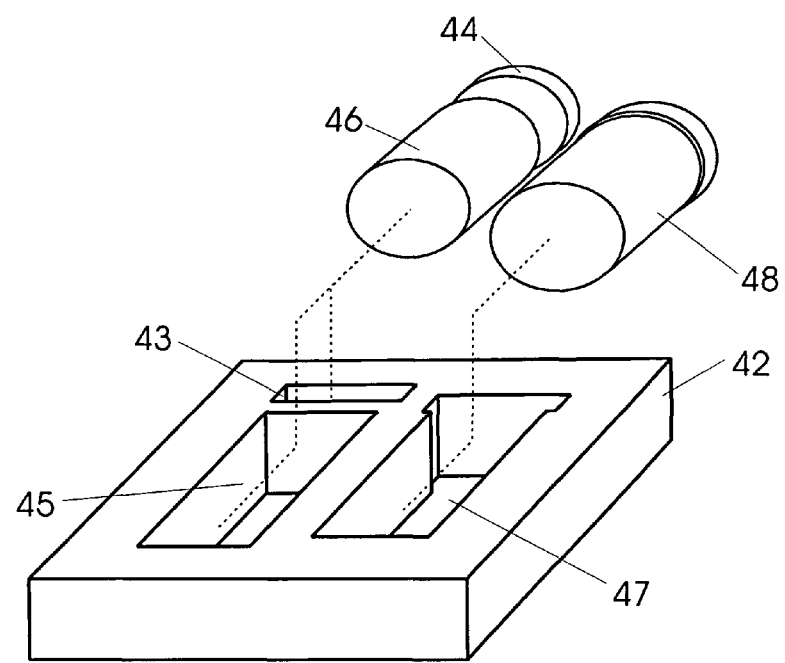
Figure 4:
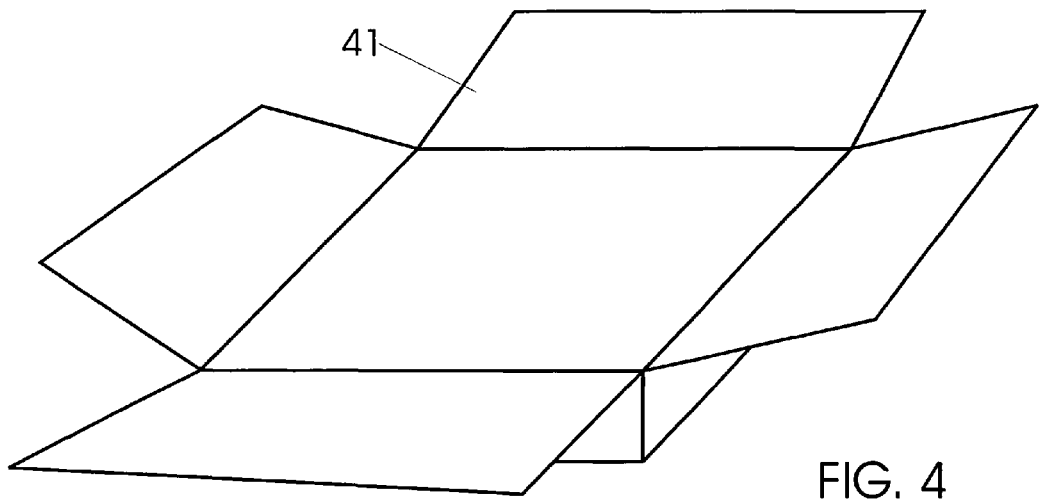

FIGS. 2 and 3 further illustrate important aspects of these systems including the coupling between a sealing cap 21 and receiving vessel 22. By way of counter-rotation (indicators 23) about a common axis, a cap is screwed on to a receiving vessel to couple therewith. As the cap is turned, the thread set causes the cap to advance towards (indicated by 24) the receiving vessel along the axis. As the reservoir 25 containing preserving fluid therein advances to the knife 26 and comes into contact therewith, the thin-film 27 is pierced 31 to release the fluid 32 whereby it passes into the receiving vessel to mix with collected saliva 33. In addition, the cap is further advanced such that a liquid-tight seal is formed between the annular flange of the sealing cap 34 and an inside surface 35 of the receiving vessel which forms a cooperating seat. A pressure between these two elements assures liquid is securely contained within the receiving vessel for a durable and long-term storage.

One important aspect of these systems relates to use of the apparatus during a collection step. As the quantity of saliva a required tends to be more than what might be obtained in a single 'spit' action, a donor is required to a repeatedly spit into the funnel aperture. For this reason, it is desirable that the apparatus can be placed on a flat surface to rest between spits. To provide for this, a outer tube fashioned as a rigid body is shaped with a base for 'foot' portion to assure the vessel is held upright when resting on a table. While the base may include an opening at its bottom, at least an annular ring which lies substantially in a plane provides a resting surface for these devices. Some versions may include a flared lip on the body to increase the surface area of the annulus for improved stability.

The rigid body is sometimes transparent or translucent for an attractive 'clean' feel and may be formed of molded plastic. In addition, its outside surface may be scored or scuffed to provide for an improved grip and handling. As some molded plastics are left quite smooth after formation, it is sometimes desirable for these apparatus to prepare the outside surface of the body has a 'gripping' surface economically suitable for being handled easily by human fingertips.

A reservoir is preferably integrated within an interior cavity portion of the cap element. The reservoir may be formed integrally with the cap in a plastic molding step. It is preferably cylindrical in shape and approximately 1 cm deep. The reservoir may be filled with a preserving fluid by automated machinery, and thereafter the reservoir may be sealed to contain and protect the fluid until it is required for use. In anticipated systems, a reservoir may contain a specially prepared bonding surface to which a thin-film or foil may be affixed for example by adhesives or plastic weld. A thin-film or foil is used to complete the reservoir cell. As these support functionality related to release of the fluid from the reservoir at the appropriate time. Namely, when a cap element is coupled to the receiving vessel element, it is desirable to automatically have the fluid mixed with the saliva. Accordingly, without taking any extra steps, measuring, pouring, calculation, et cetera, an unskilled user preserves the saliva sample merely by screwing the cap to the receiving vessel together.

In one preferred version, the in a preserving fluid contained in the reservoir is colored with a dye agent. This yields a mechanism by which a user can easily determine that the foil seal was appropriately compromised and that the fluid previously contained in the reservoir has been released therefrom and has further mixed with the saliva sample. In systems where a dye is not used, it has been observed that failure due to malfunction of the foil piercing system went undetected in the sample subsequently was spoiled. Another important component of these saliva collection systems includes a special dual-mode shipping container. As these systems are specifically configured for use directly by consumers, for example at a consumer's private home, it is advantageous to provide for two-way shipping in a container suitable for same. A box 41 may have inserted therein a foam core element 42. The shipping container including this foam core element by way of cut-out cavities therein supports two discrete shipping modes. When a saliva sample collection device in accordance with this invention is shipped to a customer, it is necessary that the cap and receiving vessel be held separate to protect the contents of the fluid reservoir against being released. Accordingly in this first shipping mode a first cut-out cavity 43 is provided to accommodate the cap 44 containing the reservoir therein, while a second cut-out cavity 45 is provided to accommodate the receiving vessel 46. Once inserted accordingly, the cap and receiving vessel are held isolated spatially thereby maintaining the integrity of the reservoir. After use, and once a cap is tightly coupled with a receiving vessel and fluid has been released from its containment in the reservoir, the combined cap and receiving vessel 48 may be inserted into another cut-out cavity 47 provided specifically for the combination such that the system including the sample mixed with preserving fluid may be return shipped to the laboratory. In this manner, the shipping box is particularly arranged to cooperate with the objective of releasing the preserving fluid only after use. Additionally, both shipping modes are supported by a single container and no waste material remains.

In accordance with each of preferred embodiments of the invention, saliva collection preservation and conveyance systems are provided. It will be appreciated that each of the embodiments described include an apparatus and that the apparatus of one preferred embodiment may be slightly different than the apparatus of another embodiment. Accordingly, limitations read in one example should not be carried forward and implicitly assumed to be part of an alternative example.

One will now fully appreciate how easy-to-use saliva sample collection systems and kits may be arranged and configured. Although the present invention has been described in considerable detail with clear and concise language and with reference to certain preferred versions thereof including best modes anticipated by the inventors, other versions are possible. Therefore, the spirit and scope of the invention should not be limited by the description of the preferred versions contained therein, but rather by the claims appended hereto.

The invention claimed is:

1. Apparatus for collection and conveyance of human saliva including DNA matter comprising two primary elements: a receiving vessel for collecting saliva and a sealing cap,
    said receiving vessel comprising: a rigid body fashioned as an outer concentric cylinder,
        an inner cylindrical tubular portion; and
        an entrance aperture for receiving saliva,
    said sealing cap having integrated therewith a fluid reservoir,
    said receiving vessel element and sealing cap element each having integrated therewith a complementary mechanical interlocking system forming a liquid-tight seal therebetween when in a coupled state, whereby
    features of the apparatus are directly integrated with either the receiving vessel element or the sealing cap element; wherein
    said rigid body has a slot hole cut therein, the slot hole being operable as a view window whereby a user may view the inner cylindrical tubular portion.

2. Collection and conveyance apparatus of claim 1, said receiving vessel further includes a ridge formed on said cylindrical tubular portion, the ridge and view window are aligned radially and axially whereby a user may easily view the ridge via said view window.

* * * * *